(12) United States Patent
Li et al.

(10) Patent No.: US 8,796,462 B2
(45) Date of Patent: Aug. 5, 2014

(54) ZEOLITIC IMIDAZOLATE FRAMEWORKS FOR KINETIC SEPARATION OF PROPANE AND PROPENE

(75) Inventors: Jing Li, Cranbury, NJ (US); Kunhao Li, Princeton, NJ (US); David H. Olson, Pennington, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 252 days.

(21) Appl. No.: 13/109,614

(22) Filed: May 17, 2011

(65) Prior Publication Data

US 2011/0282067 A1    Nov. 17, 2011

Related U.S. Application Data

(60) Provisional application No. 61/345,315, filed on May 17, 2010.

(51) Int. Cl.
  *C07F 3/06* (2006.01)
  *C07F 15/06* (2006.01)
  *C07C 7/12* (2006.01)

(52) U.S. Cl.
  CPC . *C07F 3/06* (2013.01); *C07F 15/06* (2013.01); *C07C 7/12* (2013.01)
  USPC .......................................... 548/101; 585/830

(58) Field of Classification Search
  CPC .............. C07F 3/06; C07F 15/06; C07C 7/12
  USPC .......................................... 548/101; 585/830
  See application file for complete search history.

(56) References Cited

FOREIGN PATENT DOCUMENTS

WO    WO 2008/140788 A1 * 11/2008   ............. C01B 39/00

OTHER PUBLICATIONS

Li et al. "Zeolitic Imidazolate Frameworks for Kinetic Separation of Propane and Propene" Journal of the American Chemical Society, 2009, vol. 131, pp. 10368-10369.*
Hayashi et al., "Zeolite A imidazolate frameworks", Letter, Nature Materials, Jul. 2007, vol. 6, pp. 501-506.
Tian et al., "Design and Generation of Extended Zeolitic Metal-Organic Frameworks (ZMOFs): Synthesis and Crystal Structures of Zinc(II) Imidazolate Polymers with Zeolitic Topologies", Chem. Eur. J. 2007, vol. 13, pp. 4146-4154.
Baburin et al., "Enumeration of Not-Yet-Synthesized Zeolitic Zinc Imidazolate MOF Networks: A Topological and DFT Approach". J. Phys. Chem. B 2008, vol. 112, pp. 9437-9443.
Wang et al, "Colossal cages in zeolitic imidazolate frameworks as selective carbon dioxide reservoirs", Letters, Nature, May 2008, vol. 453, pp. 207-211.
Banerjee et al, High-Throughput Synthesis of Zeolitic Imidazolate Frameworks and Application to CO2 Capture, Science vol. 319, Feb. 2008, pp. 939-943.
Morris et al., "Crystals as Molecules: Postsynthesis Covalent Functionalization of Zeolitic Inidazolate Frameworks", J. AM. Chem. Soc., 2008, vol. 130, pp. 12626-12627.
Wu et al., "New Zeolitic Imidazolate Frameworks: From Unprecedented Assembly of Cubic Clusters to Ordered Cooperative Organization of Complementary Ligands", Chem. Mater., 2008, vol. 20, pp. 7377-7382.
Wu et al., "A New Zeolitic Topology with Sixteen-Membered Ring and Multidimensional Large Pore Channels", Chem. Eur. J. 2008, vol. 14, pp. 7771-7773.
Wu et al., "Hydrogen Storage in a Prototypical Zeolitic Imidazolate Framework-8", J. AM. Chem. Soc. 2007, vol. 129, pp. 5314-5315.
Zhou et al., "Quasi-Free Methyl Rotation in Zeolitic Imidazolate Framework-8", J. Phys. Chem. A 2008, vol. 112, pp. 12602-12606.
Zhang et al., "Eight coordination with bis(bidentate) bridging ligands: zeolite topology versus square grid networks", Chem. Commun., 2008, pp. 847-849.
Liu et al., "Understanding the Adsorption and Diffusion of Carbon Dioxide in Zeolitic Imidazolate Frameworks: A Molecular Simulation Study", J. Phys. Chem. C 2009. vol. 113, pp. 5004-5009.
Cravillon et al., "Rapid Room-Temperature Synthesis and Characterization of Nanocrystals of a Prototypical Zeolitic Imidazolate Framework" Chem. Mater. 2009, vol. 21, pp. 1410-1412.
Banerjee et al., "Control of Pore Size and Functionality in Isoreticular Zeolitic Imidazolate Frameworks and their Carbon Dioxide Selective Capture Properties", J. Am. Chem. Soc. 2009, vol. 131, pp. 3875-3877.
Zhang et al., "Zeolitic Boron Imidazolate Frameworks", Angew. Chem. Int. Ed. 2009, vol. 48, pp. 2542-2545.
Huang et al., "Ligand-Directed Strategy for Zeolite-Type Metal-Organic Frameworks: Zinc(ii) Imidazolates with Unusual Zeolitic Topologies", Angew. Chem. Int. Ed. 2008, vol. 45, pp. 1557-1559.
Park et al., "Exceptional chemical and thermal stability of zeotitic imidazolate frameworks", PNAS, Jul. 2006. vol. 103. No. 27, 10188-10191.
Lamia et al., "Adsorption of propane, propylene and isobutane on a metal-organic framework: Molecular simulation and experiment", Chemical Engineering Science, 2009, vol. 64, pp. 3246-3259.

* cited by examiner

*Primary Examiner* — Joseph Kosack
(74) *Attorney, Agent, or Firm* — Fox Rothschild LLP

(57) ABSTRACT

Zeolitic Imidazolate Frameworks (ZIFs) characterized by organic ligands consisting of imidazole ligands that are either essentially all 2-chloroimidazole ligands or essentially all 2-bromoimidazole ligands are disclosed. Methods for separating propane and propene with the ZIFs of the present invention, as well as other ZIFs, are also disclosed.

12 Claims, 12 Drawing Sheets

ZEOLITIC IMIDAZOLATE FRAMEWORKS FOR KINETIC SEPARATION OF PROPANE AND PROPENE

CROSS-REFERENCE TO RELATED APPLICATION

The present application claims the benefit of priority under 35 U.S.C. §119(e) of U.S. Provisional Application No. 61/345,315, filed on May 17, 2010, the entire disclosure of which is incorporated herein by reference.

STATEMENT REGARDING FEDERALLY SPONSORED RESEARCH OR DEVELOPMENT

The invention was made with government support under Contract No. DE-FG02-08ER46491, awarded by the Department of Energy. The government has certain rights to this invention.

BACKGROUND OF THE INVENTION

Industrial olefin/paraffin separations heavily rely upon energy-intensive cryogenic distillation-based techno-logies, which represent a class of the most important and also the most costly processes in the chemical industry.

Adsorptive separation is widely considered as a more energy- and cost-efficient alternative. The structures and properties of the adsorbent materials often dictate the separation mechanisms that apply: molecular sieving or steric size exclusion, equilibrium- or kinetics-based separation. While most adsorbents (exclusively zeolites or amorphous adsorbents) studied for olefin/paraffin separations achieve such separations by their preferential equilibrated uptake of one component versus the other or by size exclusion, there are a limited number of cases where the separations are accomplished by differences in the diffusion rates of the adsorbates (olefin and paraffin) into and out of the adsorbents.

Accordingly, there is a need for additional compounds and methods useful for gas separation.

SUMMARY OF THE INVENTION

This need is met by the microporous metal organic frameworks provided by the present invention. Zeolitic Imidazolate Frameworks (ZIFs) have now been discovered for which propane and propene have significantly different rates of diffusion, thereby providing an energy- and cost-efficient means to separate the two gases. In particular, the present invention incorporates the discovery that using 2-chloro-imidazole or 2-bromoimidazole as the imidazole ligand of the organic portion of the metal organic framework in a ZIF results in a ZIF with a pore opening size effective to separate propane and propene based on their significantly different relative diffusion rates.

Therefore, according to one aspect of the present invention, a Zeolitic Imidazolate Framework is provided in which the imidazole ligands are either essentially all 2-chloroimidazole or essentially all 2-bromoimidazole. ZIF embodiments according to this aspect of the invention include ZIFs in which the metal portion of the metal organic framework includes Zn(II) and ZIFs in which the metal portion of the metal organic framework includes Co(II).

It has further been discovered that a previously-reported ZIF using 2-methyl imidazole as the imidazole ligand also has a pore opening size effective to separate propane and propene based on significantly different rela-tive diffusion rates.

Therefore, according to another aspect of the present invention, a method is provided for the separation of propane and propene, which includes the steps of (1) providing a bed containing a Zeolitic Imidazolate Framework (ZIF) in which the imidazole ligands are either essentially all 2-chloroimidazole, essentially all 2-bromo-imidazole or essentially all 2-methylimidazole; (2) contacting the bed with a mixture of propane and propene for a period of time and at a temperature and pressure sufficient for the ZIF to adsorb a propene-enriched mixture of propane and propene, thereby decreasing the concentration of propene in the non-adsorbed mixture of propane and propene; and (3) collecting the non-adsorbed mixture of propane and propene in which the propene content has been decreased.

One embodiment according to this aspect of the inventive method further includes the step of (4) collecting the propene-enriched mixture of propane and propene adsorbed onto the ZIF. Another embodiment according to this aspect of the inventive method further includes the step of re-circulating the collected non-adsorbed mixture of propane and propene back to the bed to further decrease the concentration of propene in the mixture.

Another embodiment according to this aspect of the inventive method further includes the step of re-circulating the collected adsorbed propene-enriched mixture of propane and propene back to the bed to further increase the concentration of propene in the enriched mixture. Other embodiments according to this aspect of the invention use ZIFs in which the metal portion of the metal organic framework includes Zn(II), and ZIFs in which the metal portion of the metal organic framework includes Co(II).

A more complete appreciation of the invention and many other intended advantages can be readily obtained by reference to the following detailed description of the preferred embodiments and claims in conjunction with the accompanying drawings, which disclose the principles of the invention and the best modes that are presently contemplated for carrying them out.

DETAILED DESCRIPTION OF PREFERRED EMBODIMENTS

Microporous metal organic frameworks (MMOFs) as a new type of crystalline adsorbent materials, such as zeolytic imidazolates, have shown great potential in hydrocarbon separations. It has now been discovered that certain MMOFs are capable of kinetic separation of propane and propene, which is one of the most difficult chemical separations due to their very close relative volatilities and molecular sizes.

MMOFs according to the present invention belong to a recently emerged group of materials named Zeolitic Imidazolate Frameworks (ZIFs). Their structures are constructed upon metals of tetrahedral coordination geometry (e.g., $Zn^{II}$ and $Co^{II}$) and imidazole ligands and closely resemble the structures of zeolites.

In addition to their excellent thermal and chemical stability, they also lack Lewis acid and Brønsted acid sites that may catalyze polymerization of olefins inside the pores. For true zeolites, only those with a high silica content can be used for separation of olefin/paraffin, whereas their synthesis can be difficult.

Reacting $Zn(NO_3)_2.6H_2O$ with 2-chloroimidazole (2-cim) or 2-bromoimidazole (2-bim) in methanol under solvothermal conditions resulted in good quality polyhedral crystals of $[Zn(2-cim)_2].2.1(CH_3OH)$ (Compound 1) and $[Zn(2-bim)_2].0.16(H_2O).0.16(C_2H_5OH)$ (Compound 2), respectively. Single crystal X-ray diffraction revealed that Compounds 1 and 2 are iso-structural to each other, both crystallizing in the cubic I43m space group with almost identical unit cell constants. $Zn^{II}$ centers are invariably tetrahedrally coordinated to four N atoms from four imidazolate ligands. Each imidazole coordinates to two $Zn^{II}$, with Zn-Im-Zn angles ($\theta$, FIG. 1d) close to 145°, which are coincident with the typical Si—O—Si angles found in many zeolites.

Figure 1A:
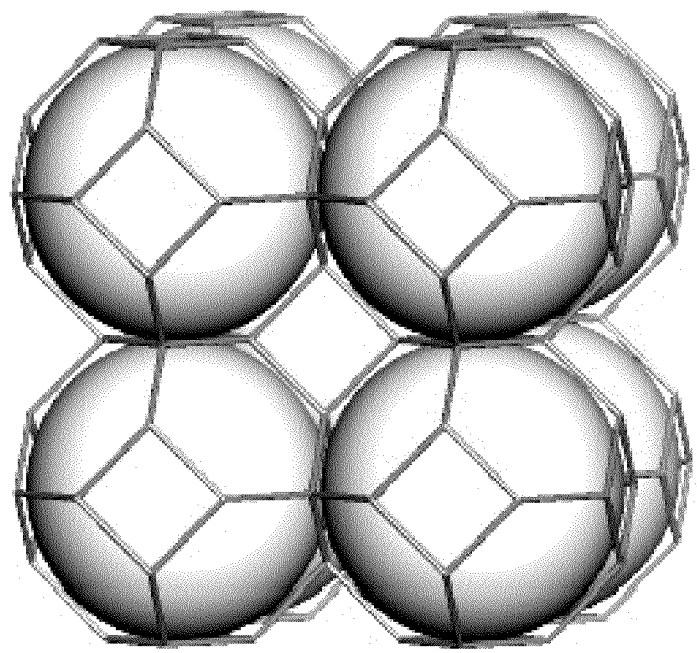
FIG. 1 illustrates the expanded sodalite (sod) framework of a ZIF according to one embodiment of the present invention, formed by connecting the tetrahedral $Zn^{II}$ centers (a); a space-filling model of one sod cage (b); a view of the pore opening along one 3-fold axis (c); and a labeling scheme of the structural features determining the pore opening size (d)
Figure 1B:
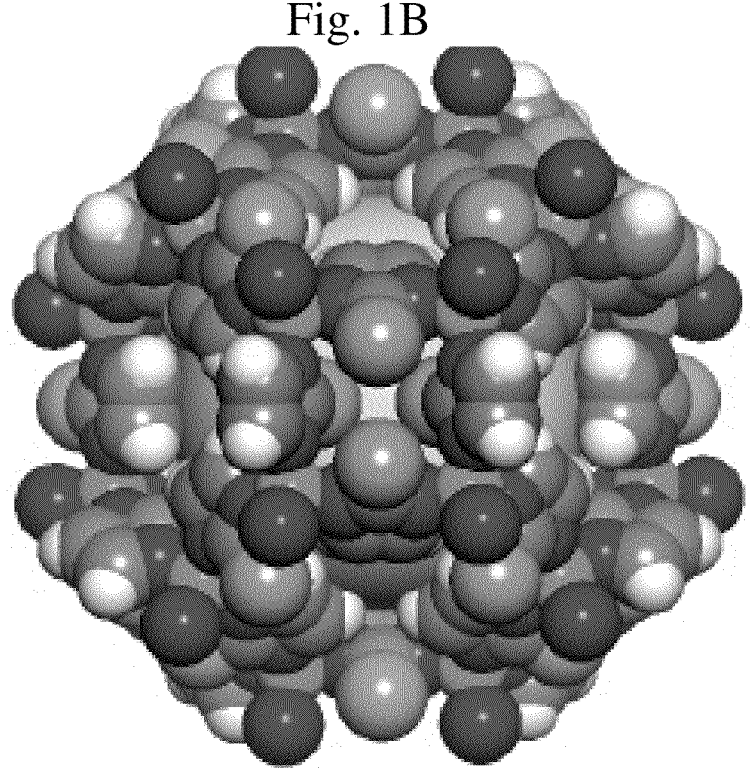
Figure 1C:
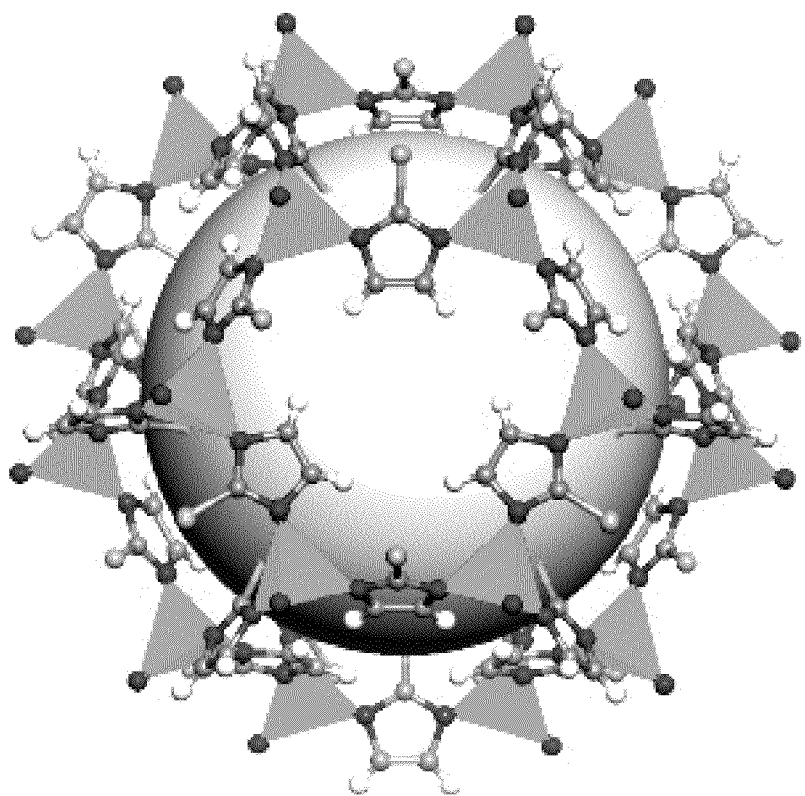
Figure 1D:
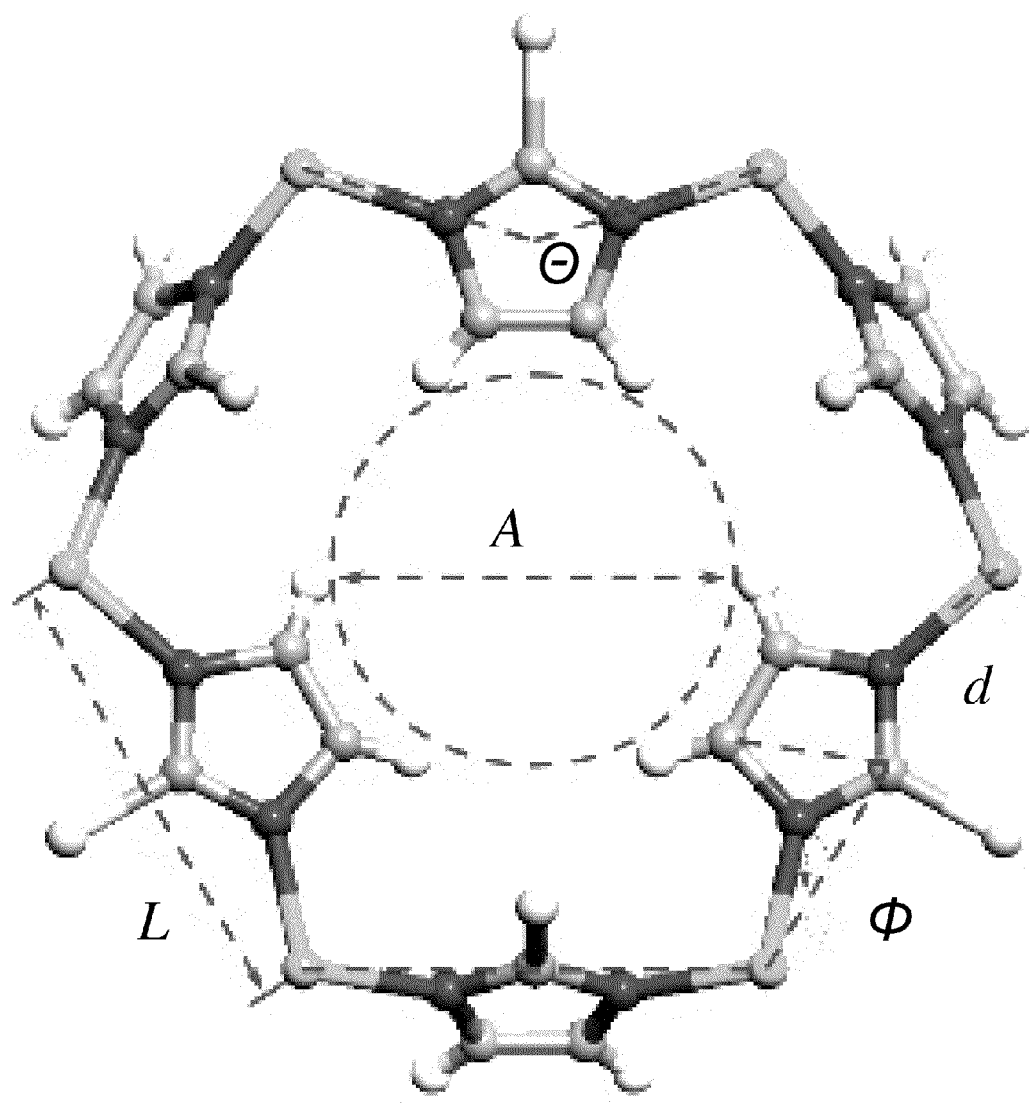

This geometry has been reasonably attributed to be the main structural directing factor in the formation of zeolite-like frameworks. In this case, both Compounds 1 and 2 have an expanded sodalite (sod) framework structure (FIG. 1a). The square faces of the truncated octahedral cages are essentially blocked by the chlorine or bromine atoms (FIG. 1b); therefore, the cages are interconnected along 3-fold axes through the small openings delimited by H atoms on imidazolate ligands (FIG. 1c).

Compounds 1 and 2 are isostructural to the recently reported ZIF-8 structure (Compound 3, with 2-methyl-imidazole as the ligand). The slight differences in the sizes of the three substituents (and possibly in combi-nation with their different electronic inductive effects) lead to small but significant perturbations to the Zn—N bond distances (d), Zn-Im-Zn angles ($\theta$) and the dihedral angles between the imidazole ring and the hexagonal faces enclosed by 6 $Zn^{II}$ centers ($\Phi$), and Zn—Zn distances (L), which result in different effective pore opening (aperture) sizes (A, FIG. 1d and Table 1). All disordered solvent molecules were removed for clarity. Spheres indicate the cavity inside the cages (12.5 Å in diameter).

TABLE 1

Structural Factors Determining the Effective Size of Pore Openings, A (Excluding van der Waals Radius of H)

| | $\theta$ (deg) | d (Å) | $\Phi$ (deg) | L (Å) | A (Å) |
|---|---|---|---|---|---|
| 1 | 142.62 | 1.983 | 5.328 | 6.004 | 3.37 |
| 2 | 144.35 | 1.995 | 7.032 | 6.032 | 3.54 |
| 3 | 144.77 | 1.984 | 10.764 | 6.015 | 3.26 |

The present invention incorporates the discovery that seemingly small differences in effective pore opening sizes (<0.2 Å) are critical to propane/propylene ($C_3°/C_3^-$) separation capabilities.

Figure 2A:
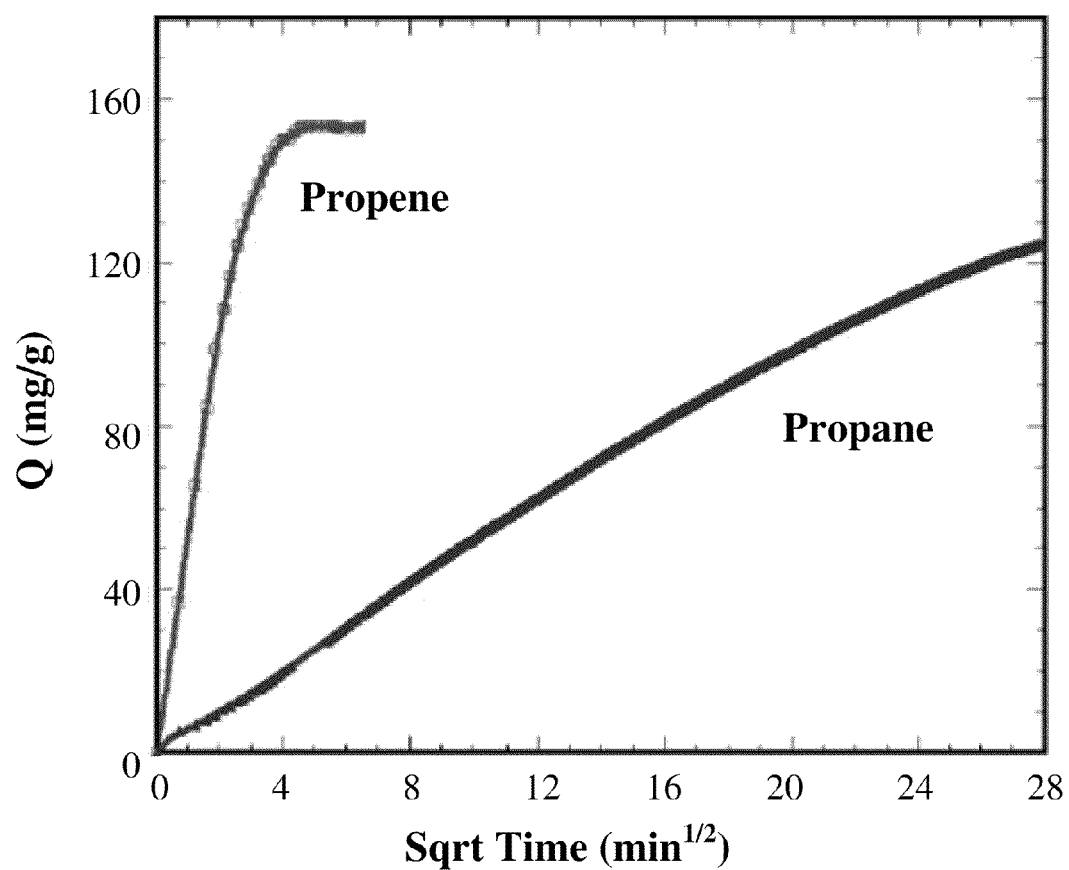
FIG. 2 demonstrates differences in propene and propane uptake by Compound 3 (A) and Compound 1 (B) as a function of square root of time.
Figure 2B:
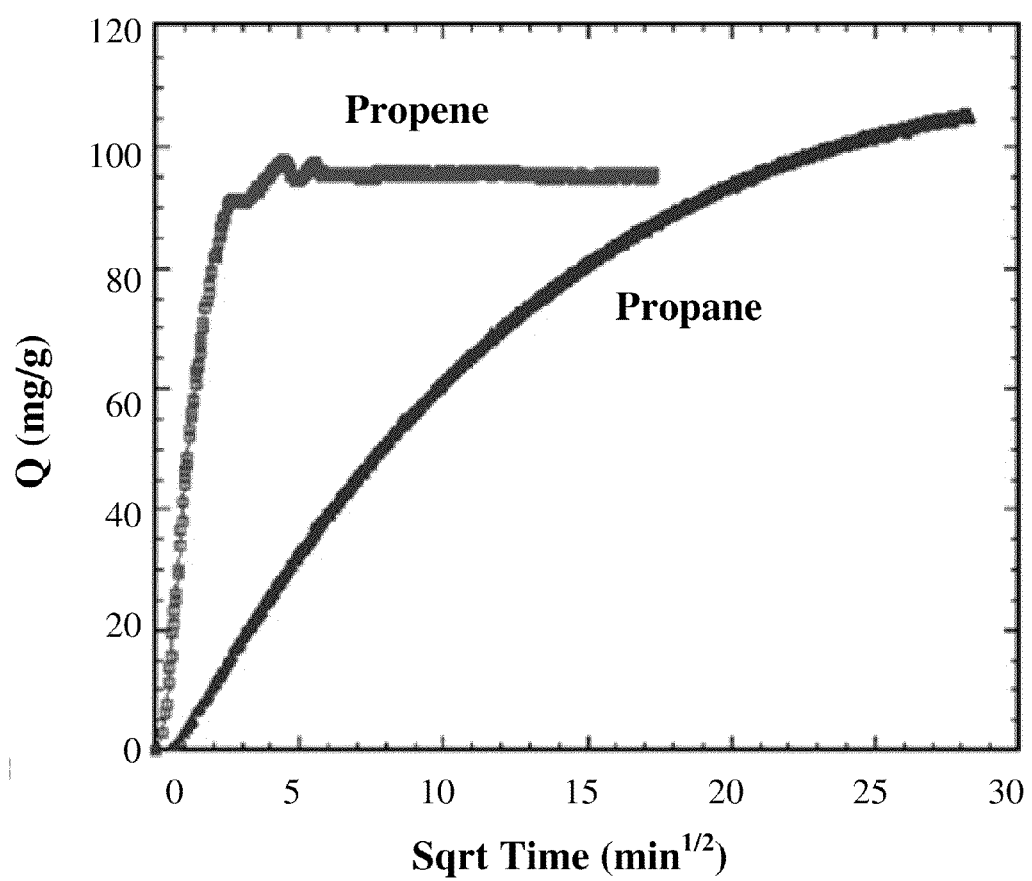

Under equilibrium conditions, propane and propene adsorption measurements on Compound 3 revealed essentially identical adsorption capacities for both, 155 and 160 mg/g at 30° C. and 600 Torr. In addition, their isosteric heats of adsorption at zero loading are similar, 34 and 30 kJ/mol, respectively. While thermodynamic separation seems impractical, the rates of adsorption are markedly different (FIG. 2). At 30° C., the ratio of their diffusion rate coefficients, $D(C_3°)/D(C_3^-)$, is 125, which is advantageous for the kinetic separation of these two very similar molecules. Adsorption rate measurements for Compound 1 have also yielded the relative adsorption rates of propene and propane. At 30° C. the ratio of their diffusion rates is 60, approximately one-half that of Compound 3 (FIG. 2).

While not being bound by any particular theory, it is believed that the separation of light hydrocarbons such as propane and propene is controlled by the critically sized pore openings. In spite of the minimal size differences of propane and propene of no more than 0.2 to 0.3 A, the energy barriers for the two molecules passing through the pore openings can be very different. The activation energies found for propene and propane are 9.7 and 74.1 kJ/mol, respectively, within Compound 1.

The lower discrimination by Compound 1 (compared to Compound 3) indicates that the propane/propene separation capability is very sensitive to the effective sizes of the pore openings. Accordingly, Compound 2 will have an even lower ratio of the diffusion rate coefficients of propene/propane due to its even larger pore opening.

It is noted that the propene (and propane) uptake rate found for Compound 3 (with crystal size ~150 μm) has not yet reached an optimum for an efficient kinetics-based pressure swing adsorption (PSA) separation process. However, smaller crystals can be prepared for faster pressure swing cycles, which should lead to more rapid kinetic separations. In one embodiment of the invention the ZIF crystal size is about 0.1 to about 1000 nm.

Figure 9:
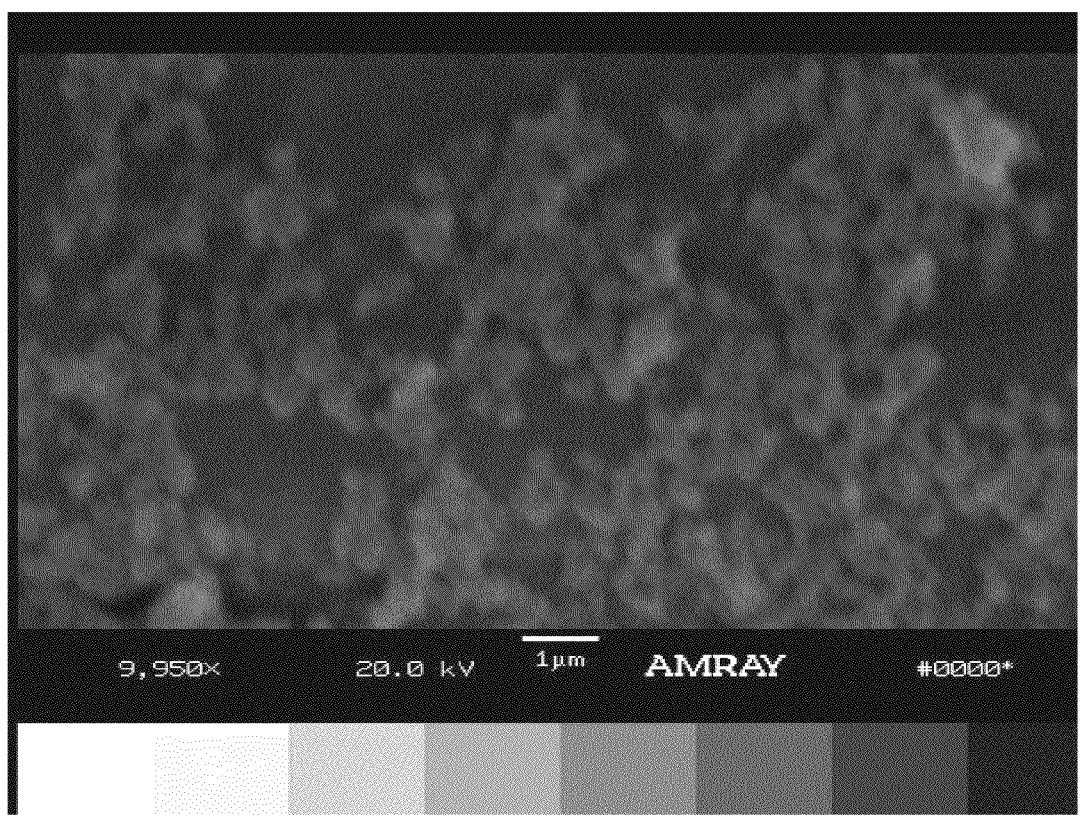
FIG. 9 illustrates the scanning electron microscope image of Compound 3A.

In one embodiment, nanometer-sized crystals of compound 3 were synthesized by rapidly pouring an aqueous solution of $Zn(NO_3)_2.6H_2O$ into an aqueous solution of 2-methylimidazole, followed by isolation of compound 3 by centrifugation. The compound was obtained as a white, microcrystalline powder (FIG. 9).

In summary, the single-component diffusion rate study reveals that kinetic separation of propane and propene can be achieved using a series of metalimidazolate zeolitic framework materials, based on the remarkable differences in diffusion rates of the gases through the pore systems. The effective size of the pore opening appears to be the controlling factor determining the separation capability.

Embodiments of the invention are described in the following non-limiting examples.

EXAMPLES

Example 1

Synthesis of 2-chloroimidazole (2-cim)

To a 300-mL, three-neck, round-bottom flask equipped with a magnetic stirrer and argon inlet, were added N-tritylimidazole (3.14 g, 0.01 mol) and anhydrous THF (140 mL). The stirrer was started, and the solution was cooled to −78° C. (acetone/dry ice). n-BuLi (2.5 M in hexanes, 8.0 mL, 0.02 mol) was added via syringe resulting in reddish solution. This solution was stirred for 60 min whereupon hexachloroethane (5.0 g, 0.021 mol) in THF (25 mL) was added in portions.

The reaction mixture was stirred for 1 additional hour and then quenched with saturated aqueous ammonium chloride (100 mL). The cooling bath was removed, and when the reaction flask reached room temperature the contents were transferred to a 500 mL separatory funnel, and extracted with ethyl acetate (50 mL×2). The organic layer was separated, washed with water and brine, and dried over anhydrous sodium sulfate.

After filtration, the solvents were evaporated under reduced pressure resulting in a slightly yellow solid. The solid was refluxed with 5% acetic acid in methanol (75 mL) for 24 hours. Upon evaporation of the solvent, water was added to the residue. Extraction with hexanes effectively removed the triphenylmethane impurity. Evaporation of water in vacuo afforded off-white solid as pure 2-chloroimidazole (2-cim, 0.70 g, 69% overall yield from N-triylimidazole).

Example 2

Crystal Growth of Compounds 1-3

Figure 4:
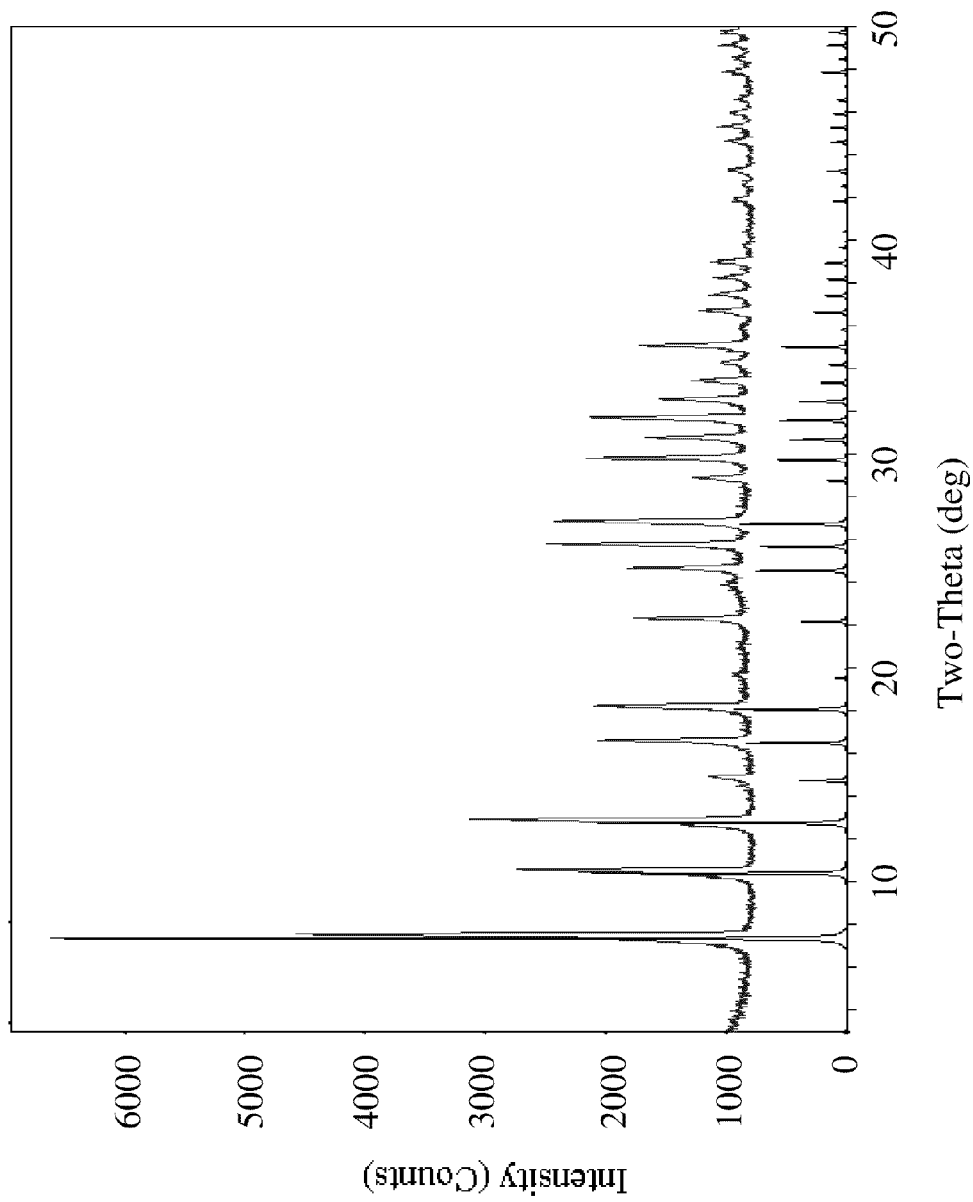
FIG. 4 illustrates the calculated (lower pattern) and observed X-Ray diffraction patterns for Compound 1.
Figure 5:
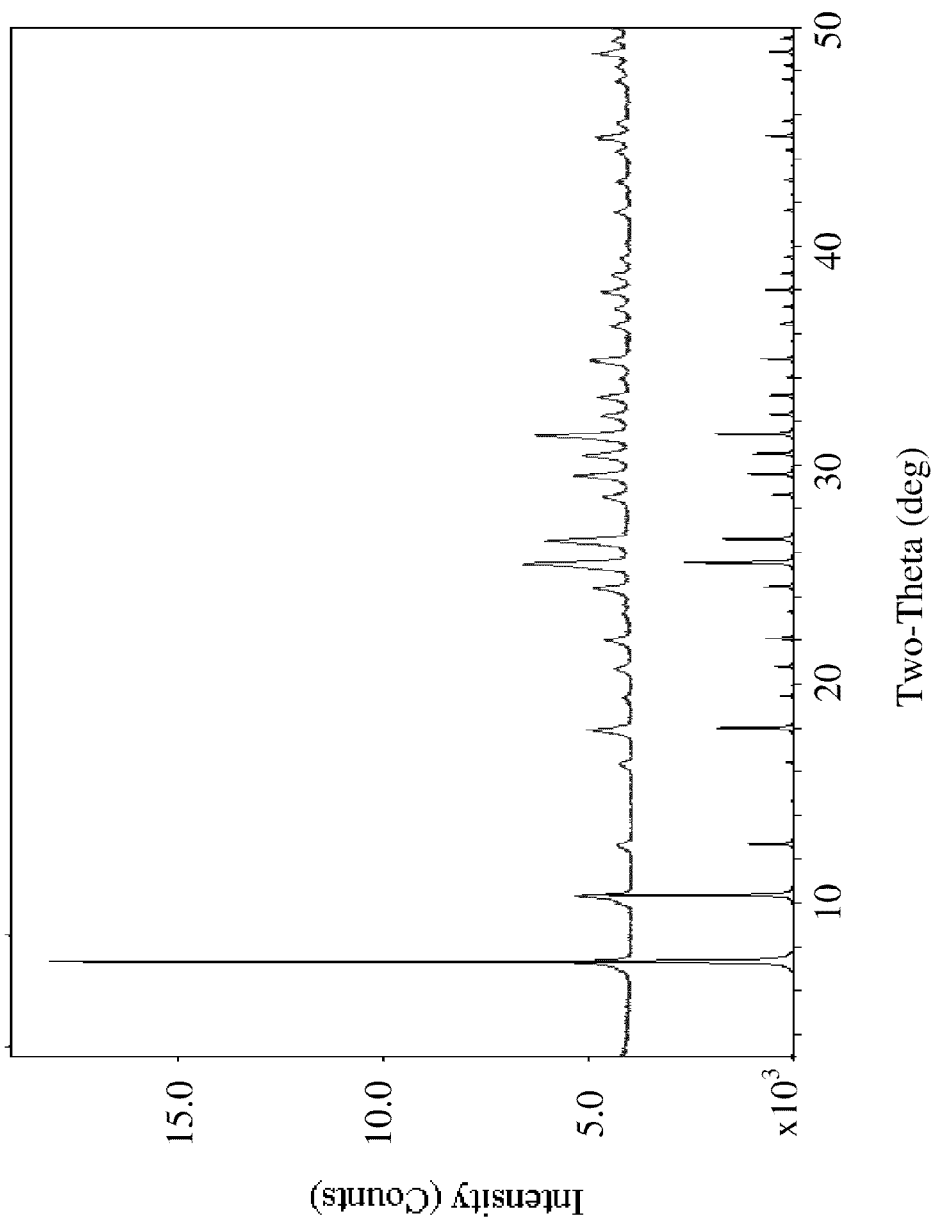
FIG. 5 illustrates the calculated (lower pattern) and observed X-Ray diffraction patterns for Compound 2.

Zinc nitrate hexahydrate (120 mg, 0.4 mmol) and 2-cim (108 mg, 1 mmol) were added to methanol (4 mL) in a glass vial. The mixture was homogenized by sonication for 2 mins. Then the vial was capped and placed into 100° C. oven for two days. Colorless polyhedral crystals of Compound 1 (See FIG. 4) were obtained (42 mg). Similarly, crystals of Compound 2 (55 mg) were obtained (See FIG. 5) by reacting zinc nitrate hexahydrate (121 mg, 0.4 mmol) and 2-bim (120 mg, 0.8 mmol) in ethanol (95%, 4 mL) for 2 days.

Figure 3:
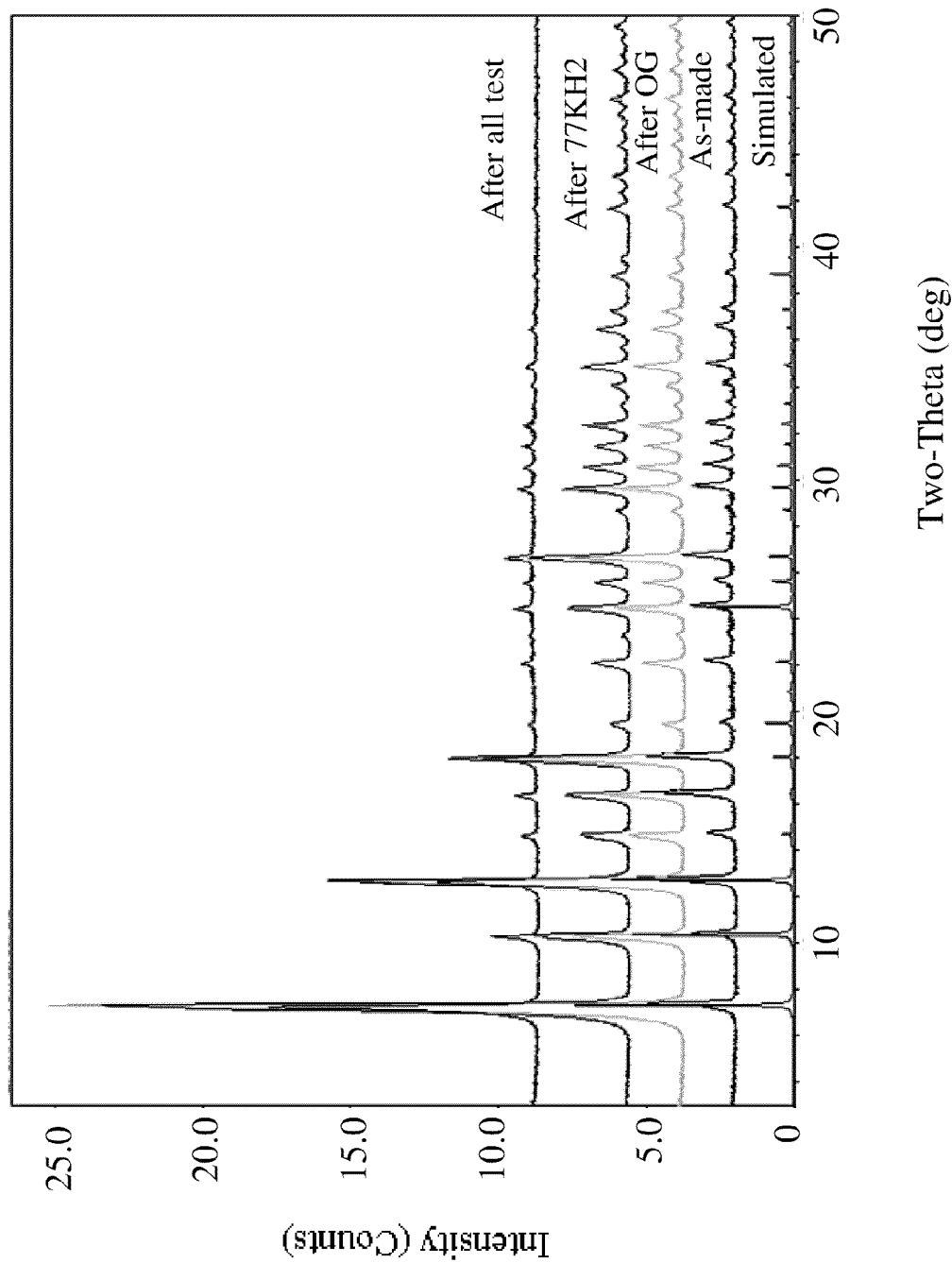
FIG. 3 illustrates the calculated (lowest pattern) and observed X-Ray diffraction patterns for Compound 3.

To a mixture of 2-methylimidazole (0.20 g, 2.5 mmol) and zinc nitrate hexahydrate (0.35 g, 1.2 mmol) in a glass vial was added N,N-dimethylformamide (DMF, 15 mL). Three drops of concentrated nitric acid was added to the suspension to obtain a clear solution. The vial was capped and placed in an isothermal oven at 120° C. for 2 days. Big polyhedral crystals of Compound 3 were obtained (40 mg, see FIG. 3).

Example 3

Selected Crystallographic and Thermal Data of Compounds 1, 2 and 3

Compounds 1-3 obtained as described in the previous examples are characterized in Tables 2-4, respectively.

TABLE 2

Crystal data and structure refinement parameters for Compound 1.

| | |
|---|---|
| Empirical formula | C8.1 H12.4 Cl2 N4 O2.1 Zn |
| Formula weight | 335.42 |
| Temperature | 100(2) K |
| Wavelength | 0.71073 Å |
| Crystal system | Cubic |
| Space group | I-43m |
| Unit cell dimensions | a = 16.9824(4) Å   α = 90°. |
| | b = 16.9824(4) Å   β = 90°. |
| | c = 16.9824(4) Å   γ = 90°. |
| Volume | 4897.8(2) Å³ |
| Z | 12 |
| Density (calculated) | 1.365 Mg/m³ |
| Absorption coefficient | 1.829 mm⁻¹ |
| F(000) | 2036 |
| Crystal size | 0.19 × 0.08 × 0.05 mm³ |
| Theta range for data collection | 1.70 to 30.49°. |
| Index ranges | −24 <= h <= 24, −23 <= k <= 24, −24 <= l <= 24 |
| Reflections collected | 21497 |
| Independent reflections | 1415 [R(int) = 0.0265] |
| Completeness to theta = 30.49° | 100.0% |

TABLE 2-continued

Crystal data and structure refinement parameters for Compound 1.

| | |
|---|---|
| Absorption correction | Semi-empirical from equivalents |
| Max. and min. transmission | 0.9141 and 0.7226 |
| Refinement method | Full-matrix least-squares on F² |
| Data/restraints/parameters | 1415/0/70 |
| Goodness-of-fit on F² | 1.009 |
| Final R indices [I > 2sigma(I)] | R1 = 0.0257, wR2 = 0.0654 |
| R indices (all data) | R1 = 0.0264, wR2 = 0.0660 |
| Absolute structure parameter | 0.005(14) |
| Largest diff. peak and hole | 0.651 and −0.243 e.Å⁻³ |

TABLE 3

Crystal data and structure refinement parameters for Compound 2.

| | |
|---|---|
| Empirical formula | C6.33 H5.33 Br2 N4 O0.33 Zn |
| Formula weight | 368.00 |
| Temperature | 100(2) K |
| Wavelength | 0.71073 Å |
| Crystal system | Cubic |
| Space group | I-43m |
| Unit cell dimensions | a = 17.065(2) Å   α = 90°. |
| | b = 17.065(2) Å   β = 90°. |
| | c = 17.065(2) Å   γ = 90°. |
| Volume | 4969.6(10) Å³ |
| Z | 12 |
| Density (calculated) | 1.476 Mg/m³ |
| Absorption coefficient | 6.284 mm⁻¹ |
| F(000) | 2088 |
| Crystal size | 0.19 × 0.08 × 0.05 mm³ |
| Theta range for data collection | 2.39 to 30.50°. |
| Index ranges | −20 <= h <= 9, −7 <= k <= 24, −19 <= l <= 24 |
| Reflections collected | 8026 |
| Independent reflections | 1434 [R(int) = 0.0558] |
| Completeness to theta = 30.50° | 99.2% |
| Max. and min. transmission | 0.7441 and 0.3814 |
| Refinement method | Full-matrix least-squares on F² |
| Data/restraints/parameters | 1434/6/56 |
| Goodness-of-fit on F² | 1.001 |
| Final R indices [I > 2sigma(I)] | R1 = 0.0320, wR2 = 0.0672 |
| R indices (all data) | R1 = 0.0398, wR2 = 0.0695 |
| Absolute structure parameter | −0.015(19) |
| Largest diff. peak and hole | 0.620 and −0.416 e.Å⁻³ |

TABLE 4

Crystal data and structure refinement parameters for Compound 3.

| | |
|---|---|
| Empirical formula | C8 H14.32 N4 O2.16 Zn |
| Formula weight | 266.60 |
| Temperature | 100(2) K |
| Wavelength | 0.71073 Å |
| Crystal system | Cubic |
| Space group | I-43m |
| Unit cell dimensions | a = 17.0629(3) Å   α = 90°. |
| | b = 17.0629(3) Å   β = 90°. |
| | c = 17.0629(3) Å   γ = 90°. |
| Volume | 4967.74(15) Å³ |
| Z | 12 |
| Density (calculated) | 1.069 Mg/m³ |
| Absorption coefficient | 1.476 mm⁻¹ |
| F(000) | 1652 |
| Crystal size | .23 × .21 × .2 mm³ |
| Theta range for data collection | 2.92 to 30.45°. |
| Index ranges | −24 <= h <= 23, −24 <= k <= 15, −14 <= l <= 15 |
| Reflections collected | 8628 |
| Independent reflections | 1410 [R(int) = 0.0330] |
| Completeness to theta = 30.45° | 99.1% |
| Absorption correction | Semi-empirical from equivalents |
| Max. and min. transmission | .889 and .812 |
| Refinement method | Full-matrix least-squares on F² |
| Data/restraints/parameters | 1410/0/45 |

TABLE 4-continued

Crystal data and structure refinement parameters for Compound 3.

| | |
|---|---|
| Goodness-of-fit on $F^2$ | 0.880 |
| Final R indices [I > 2sigma(I)] | R1 = 0.0351, wR2 = 0.1051 |
| R indices (all data) | R1 = 0.0366, wR2 = 0.1064 |
| Absolute structure parameter | −0.03(3) |
| Largest diff. peak and hole | 0.766 and −0.377 e.Å$^{-3}$ |

Example 4

Adsorption Measurement

Figure 6:
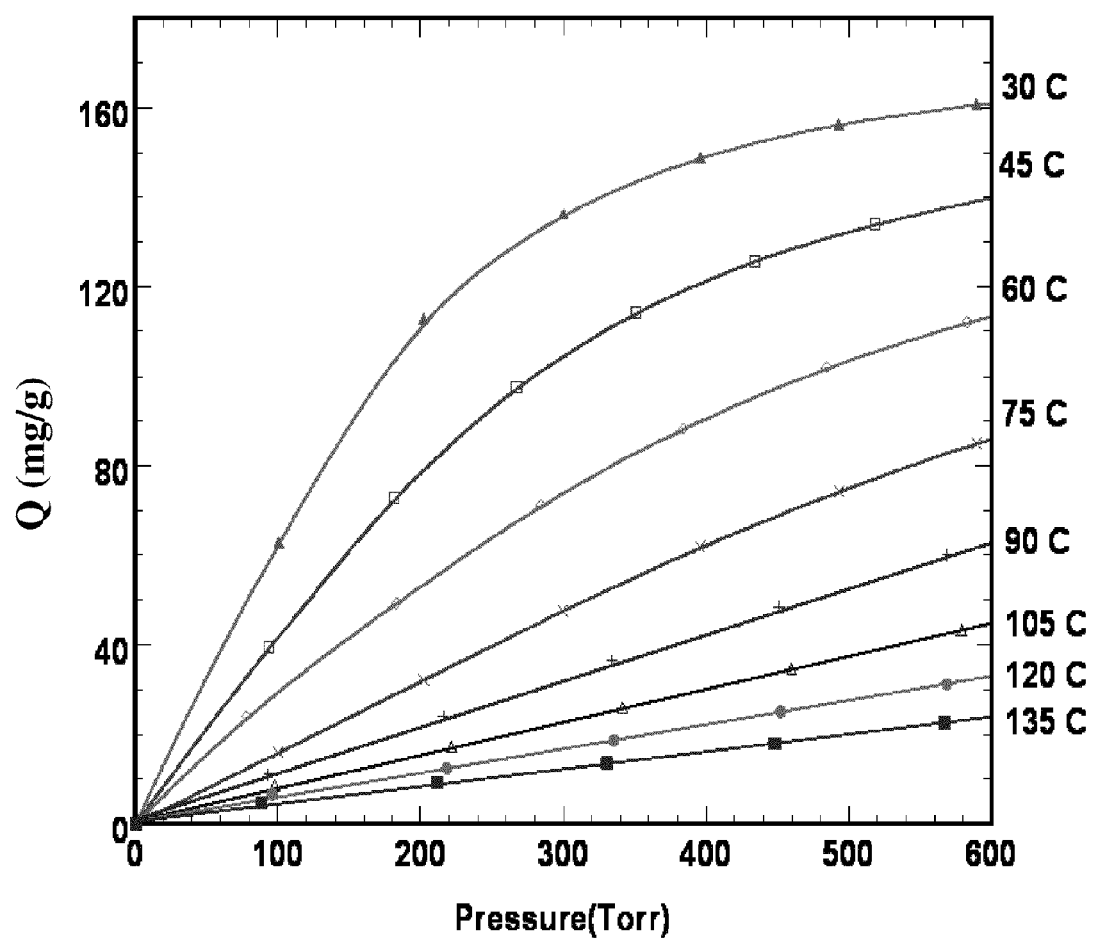
FIG. 6 illustrates propane adsorption isotherms for Compound 3 at various temperatures.
Figure 7:
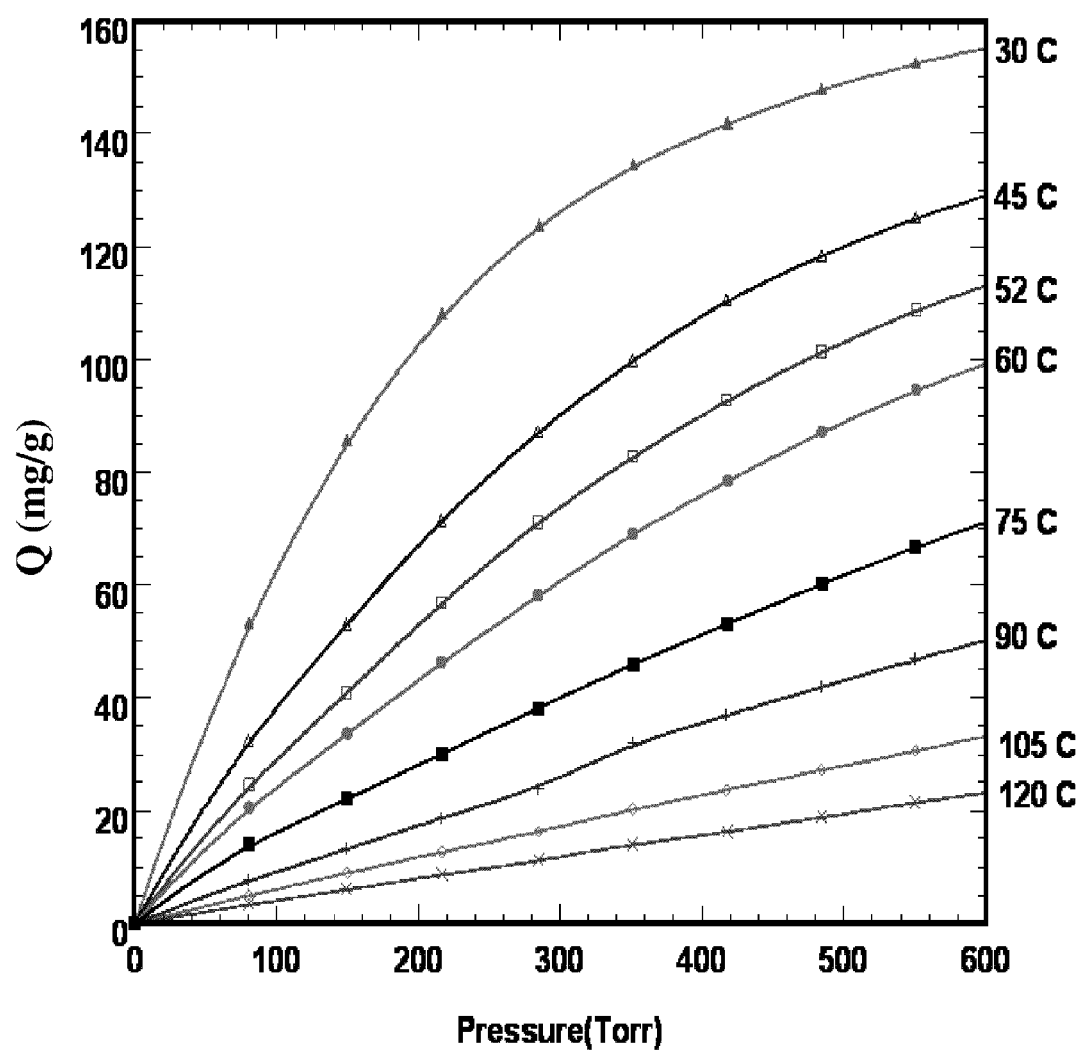
FIG. 7 illustrates propene adsorption isotherms for Compound 3 at various temperatures.

Adsorption measurements were made using a computer controlled thermogravimetric balance consisting of a TA51 electrobalance and associated TA-2000/PC control system. The gas flow through the electrobalance system was controlled via Macintosh-based LabView control soft-ware, Kinetic Systems interface, mass flow controllers and a Eurotherm temperature controller. The samples were activat-ed at 300° C. (400° C. for Compound 3) for 2 hours in dry $N_2$ prior to the sorption measurement. All isotherm data are fitted with the Langmuir equation. $D/r^2$ values are obtained by applying Crank's solution for diffusion in a plane sheet adsorbent (Crank, 1957). Adsorption results for Compound 3 are depicted in FIGS. 6 and 7.

Example 5

Synthesis of Compound 3 with Reduced Particle Size, Compound 3A

Figure 8:
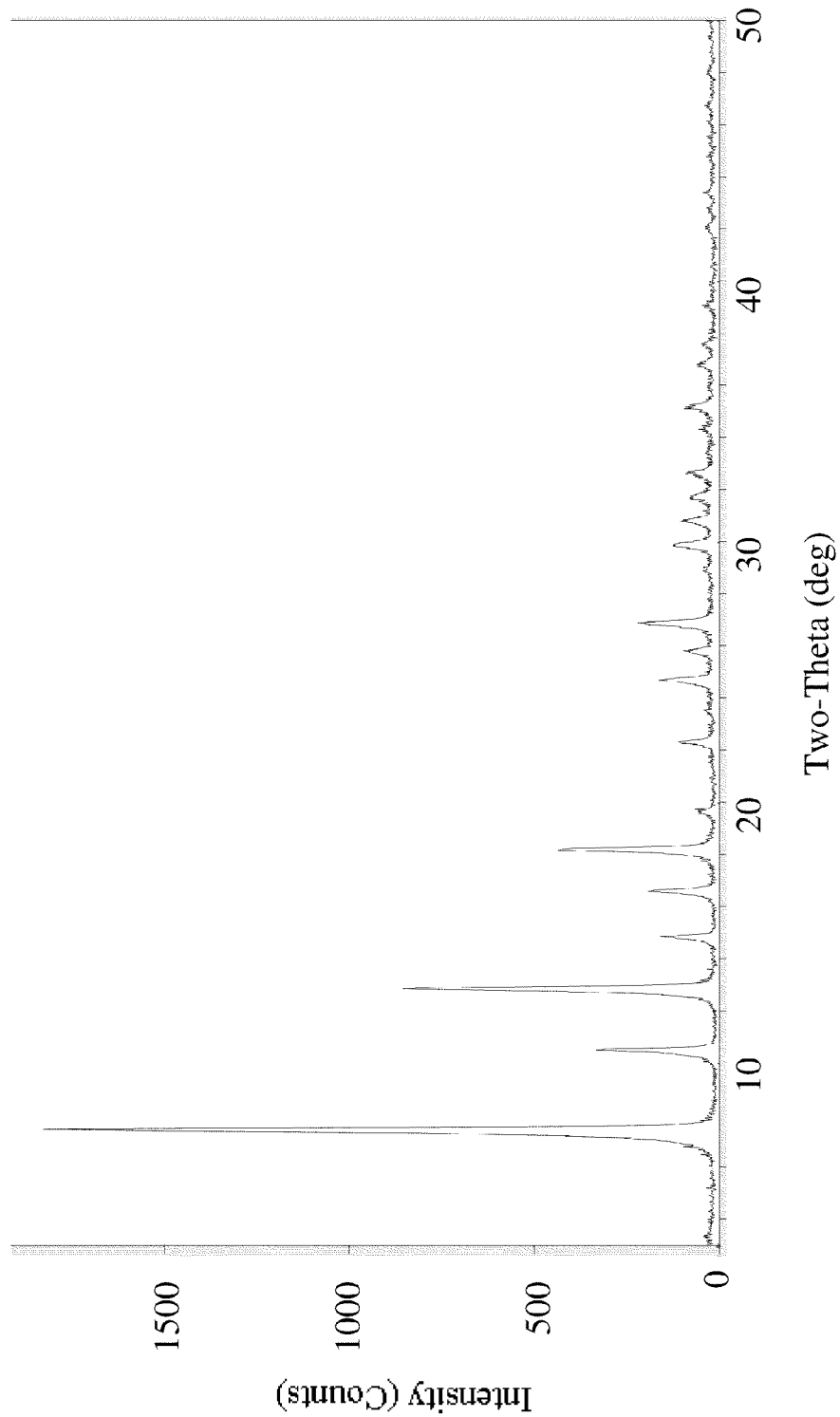
FIG. 8 illustrates the observed X-Ray diffraction pattern for Compound 3A.

Nanometer-sized crystals of Compound 3A were prepared by rapidly pouring an aqueous solution of $Zn(NO_3)_2 \cdot 6H_2O$ (0.12 g, 0.040 mmol, in 0.8 g of deionized water) into an aqueous solution of 2-methylimidazole (2.27 g, 27.6 mmol, in 8 g of deionized water), and stifling the mixture at room temperature for 5 min. The product was collected by centrifugation and was washed with deionized water four times, and dried at 60° C. for 10 h in a vacuum oven.
Sample Color: white
Sample Appearance: crystalline powder FIG. 8 shows the X-ray diffraction spectrum of Compound 3A, and FIG. 9 shows the scanning electron microscope (SEM) image of Compound 3A.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A Zeolitic Imidazolate Framework (ZIF) consisting of a metal organic framework characterized by organic ligands consisting of imidazole ligands that are either essentially all 2-chloroimidazole ligands or essentially all 2-bromoimidazole ligands.

2. The ZIF of claim 1, wherein said imidazole ligands of said metal organic framework consist of 2-chloro-imidazole.

3. The ZIF of claim 1, wherein the metal portion of said metal organic framework comprises Zn(II).

4. The ZIF of claim 1, wherein the metal portion of said metal organic framework comprises Co(II).

5. A method for the separation of propane and propene, comprising the steps of:
(1) providing a bed containing a Zeolitic Imidazolate Framework (ZIF) consisting of a metal organic framework characterized by organic ligands consisting of imidazole ligands that are either essentially all 2-chloroimidazole ligands, essentially all 2-bromoimidazole ligands or essentially all 2-methylimidazole ligands;
(2) contacting the bed with a mixture of propane and propene for a period of time and at a temperature and pressure sufficient for the ZIF to adsorb propene-enriched mixture of propane and propene, thereby decreasing the concentration of propene in the non-adsorbed mixture of propane and propene; and
(3) collecting the non-adsorbed mixture of propane and propene in which the propene content has been decreased.

6. The method of claim 5, further comprising the step of:
(4) collecting the propene-enriched mixture of propane and propene adsorbed onto the ZIF.

7. The method of claim 5, further comprising the step of: recirculating the collected non-adsorbed mixture of propane and propene back to the bed to further decrease the concentration of propene in the mixture.

8. The method of claim 5, further comprising the step of: recirculating the collected adsorbed propene-enriched mixture of propane and propene back to the bed to higher increase the concentration of propene in the enriched mixture.

9. The method of claim 5, wherein the metal portion of said metal organic framework comprises Zn(II).

10. The method of claim 5, wherein the metal portion of said metal organic framework comprises Co(II).

11. The Zeolitic Imidazolate Framework of claim 1, wherein said ZIF comprises crystals of about 0.1 nm to about 1000 nm.

12. The method of claim 5, wherein said ZIF comprises crystals of about 0.1 nm to about 1000 nm.

* * * * *